(12) United States Patent
Crook et al.

(10) Patent No.: US 7,934,687 B2
(45) Date of Patent: May 3, 2011

(54) APPENDAGE ELEVATION SUPPORT STRUCTURE

(76) Inventors: Richard A. Crook, Knoxville, TN (US); Jennifer L. Crook, Knoxville, TN (US)

(*) Notice: Subject to any disclaimer, the term of this patent is extended or adjusted under 35 U.S.C. 154(b) by 735 days.

(21) Appl. No.: 11/837,935

(22) Filed: Aug. 13, 2007

(65) Prior Publication Data
US 2009/0044731 A1   Feb. 19, 2009

(51) Int. Cl.
*F16M 11/38* (2006.01)
*A61H 1/00* (2006.01)

(52) U.S. Cl. ............... 248/168; 5/624; 5/648; 248/118; 248/177.1; 601/34; 128/845

(58) Field of Classification Search .......... 248/168–171, 248/177.1, 178.1, 179.1, 181.2, 118, 125.9, 248/218.4, 139, 143; 602/2, 4, 12, 26, 39–40; 601/29, 31, 34; 5/624, 646, 648; 128/845, 128/846, 882
See application file for complete search history.

(56) References Cited

U.S. PATENT DOCUMENTS

| | | | |
|---|---|---|---|
| 2,268,732 A | 2/1941 | Walter et al. | |
| 2,614,613 A | 6/1951 | Bushong | |
| 2,630,288 A * | 3/1953 | Eubanks, Sr. | 248/118 |
| 3,065,992 A | 11/1962 | Nagel | |
| 3,066,322 A | 12/1962 | Derby | |
| 3,264,033 A | 8/1966 | Hansburg | |
| 3,695,684 A | 10/1972 | Barberg | |
| 4,809,687 A * | 3/1989 | Allen | 602/4 |
| 4,974,830 A * | 12/1990 | Genovese et al. | 601/29 |
| 4,997,152 A * | 3/1991 | Wagman et al. | 248/168 |
| 5,290,220 A | 3/1994 | Guhl | |
| 5,509,894 A * | 4/1996 | Mason et al. | 601/34 |
| 5,794,889 A * | 8/1998 | Bailey | 244/136 |
| 5,926,882 A | 7/1999 | Veith et al. | |
| 6,012,456 A | 1/2000 | Schuerch | |
| 6,045,192 A | 4/2000 | Faulise | |
| 6,272,785 B1 * | 8/2001 | Mika et al. | 42/94 |
| 6,499,706 B1 * | 12/2002 | Sherlock et al. | 248/177.1 |
| 6,634,045 B1 | 10/2003 | DuDonis et al. | |
| 6,874,184 B2 * | 4/2005 | Chandler | 5/648 |
| 2004/0123389 A1 | 7/2004 | Boucher et al. | |

* cited by examiner

*Primary Examiner* — Tan Le
(74) *Attorney, Agent, or Firm* — Pitts & Brittian, P.C.

(57) ABSTRACT

An appendage elevation support structure is disclosed. The appendage elevation support structure includes a platform defining a central axis. A plurality of legs is secured to the platform in a substantially radial configuration about the central axis to support the platform above a surface. A frame having a plurality of support members is carried by the platform. A plurality of slings is carried and supported by the frame. The slings are adapted to cooperate to cradle and support a human appendage.

8 Claims, 7 Drawing Sheets

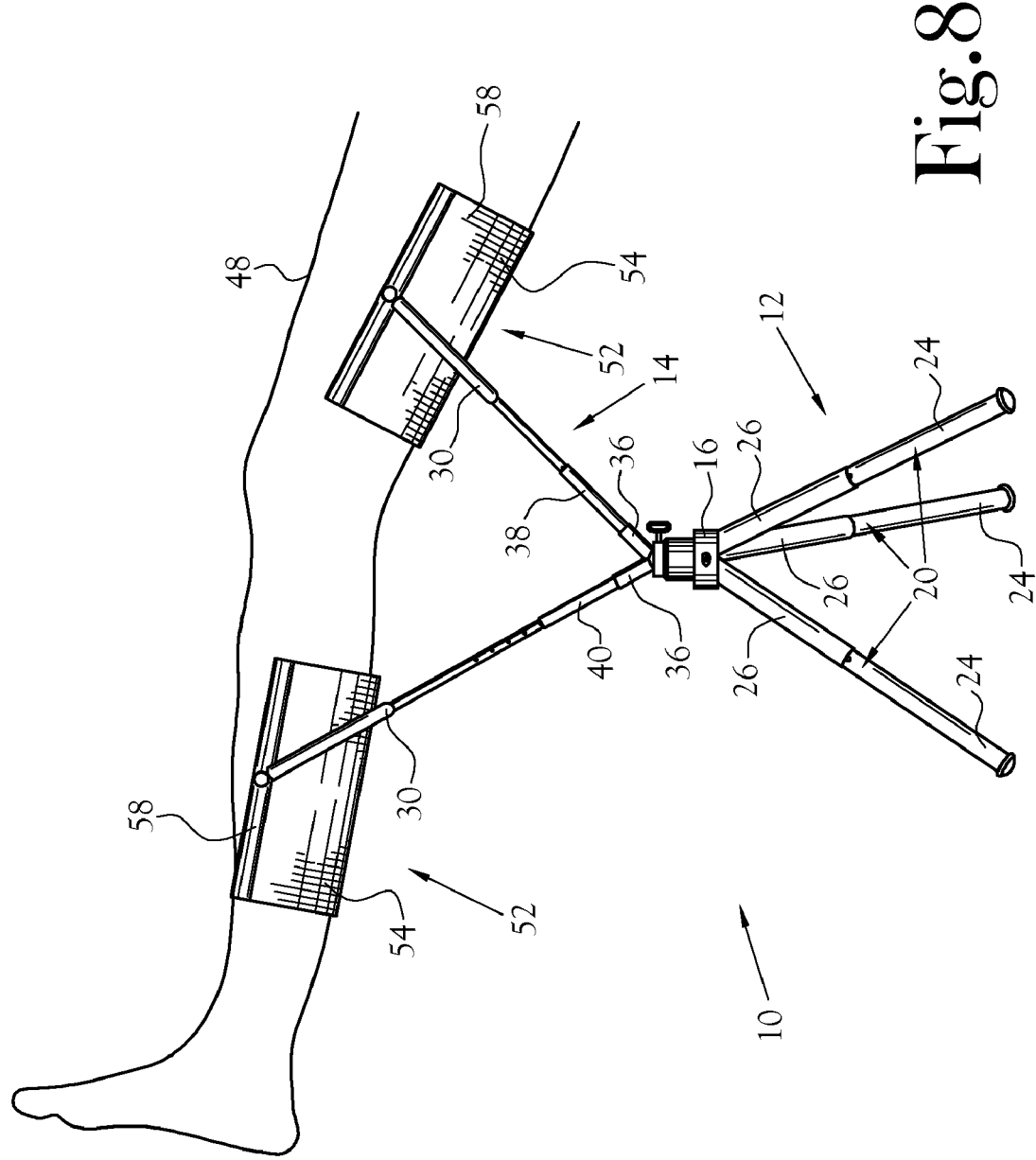

US 7,934,687 B2

APPENDAGE ELEVATION SUPPORT STRUCTURE

CROSS-REFERENCE TO RELATED APPLICATIONS

Not Applicable

STATEMENT REGARDING FEDERALLY-SPONSORED RESEARCH OR DEVELOPMENT

Not Applicable

BACKGROUND OF THE INVENTION

1. Field of Invention

The invention relates to a medical support apparatus. More particularly, this invention relates to a support apparatus for supporting and elevating appendages of a human being.

2. Description of the Related Art

Damage to the body from injury, illness, surgical procedure, or the like often results in significant lengths of time for convalescence and rehabilitation. During such convalescence and rehabilitation, treatment often mandates elevation and support of an appendage proximate the damaged portion of the body. For instance, a patient recovering from a knee surgery is often instructed to elevate and maintain the surgically-repaired knee above the patient's heart for a period of time. Such prolonged elevation typically requires a support apparatus to maintain the patient's leg in an elevated position.

In the field of medical support apparatus for maintaining a patient's appendage in an elevated position, it is often and sometimes erroneously contemplated that the patient is confined to a bed, stretcher, or the like throughout the elevation period. Therefore, various prior art structures incorporate relatively large and unwieldy support apparatus capable of being secured to a hospital bed and extended above the bed to carry and support a patient's appendage. However, in many applications, a patient desires the flexibility to temporarily suspend the elevation period and relocate, for example, from a bed to a sofa or chair, and thereafter resume the elevation period. In so doing, it is often recommended that the patient minimize the period of suspension of elevation and quickly resume elevation of the appendage in order to maximize the effectiveness of the elevation period on convalescence. In other applications, it is desirable to conveniently store the support apparatus between intervals of elevation of a patient's appendage. In all such applications, a large and unwieldy support apparatus is limited due to its inability to be conveniently disconnected, transported, or stored.

BRIEF SUMMARY OF THE INVENTION

An appendage elevation support structure is disclosed. The appendage elevation support structure includes generally a stand rotatably connected to an appendage support frame. The appendage support frame is adapted to carry and support at least one appendage.

In one embodiment, the stand includes a platform and a plurality of legs. The platform defines a central axis. Each of the plurality of legs is secured to the platform about the central axis to support the platform above a surface. A frame having a plurality of support members is carried by the platform. A plurality of slings is carried and supported by the frame. The slings are adapted to cooperate to cradle and support a human appendage.

BRIEF DESCRIPTION OF THE SEVERAL VIEWS OF THE DRAWINGS

The above-mentioned features of the invention will become more clearly understood from the following detailed description of the invention read together with the drawings in which:

FIG. 8 is a side view of the appendage elevation support structure of FIG. 5, showing the appendage elevation support structure in an extended position and supporting an appendage in a straightened position.

DETAILED DESCRIPTION OF THE INVENTION

Figure 1:
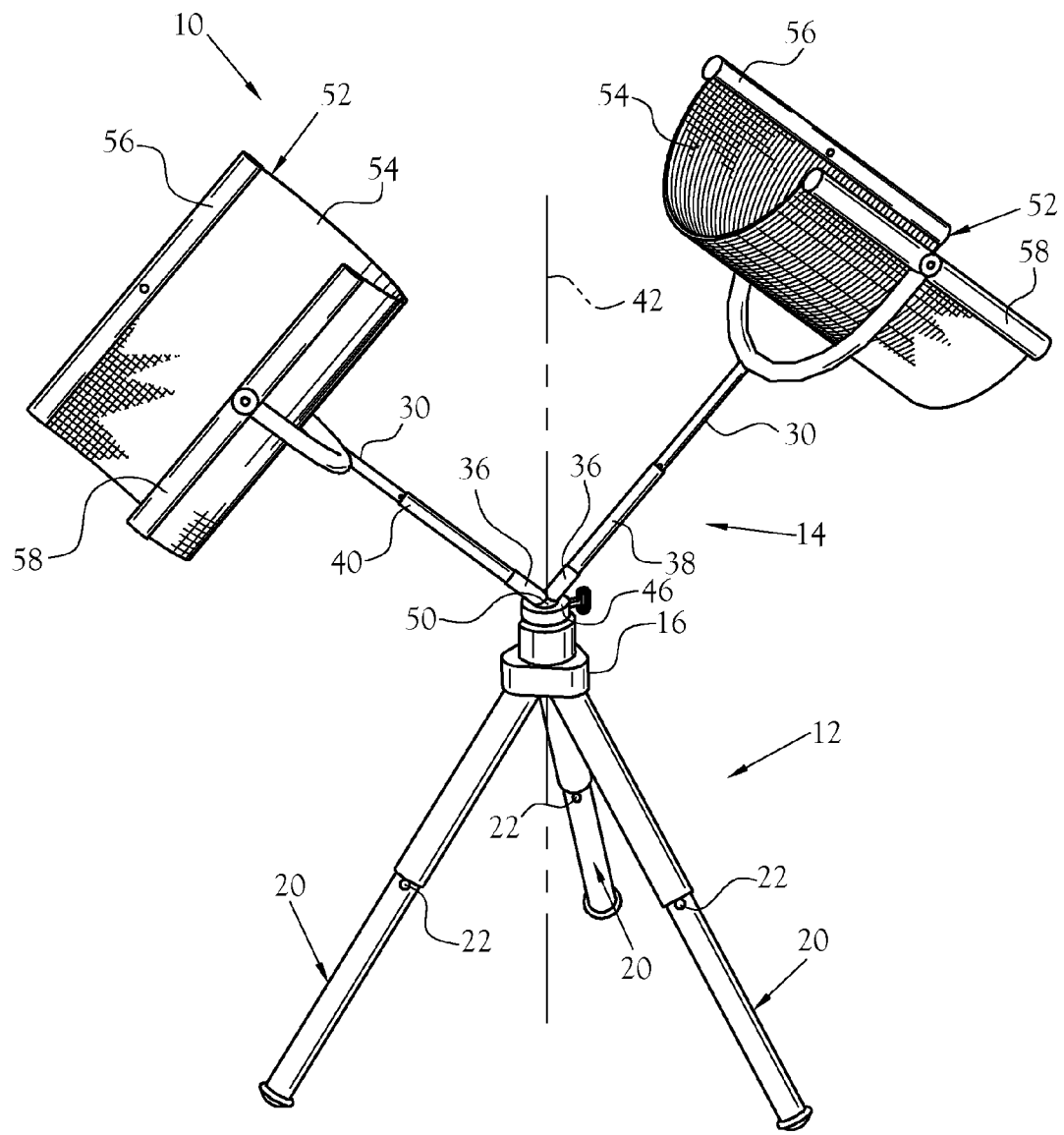
FIG. 1 is a perspective view of one embodiment of an appendage elevation support structure constructed in accordance with several features of the present invention.

FIG. 1 illustrates an appendage elevation support structure according to the present invention. The appendage elevation support structure, or structure, is identified as 10 herein and in the accompanying figures. As shown in FIG. 1, the structure 10 includes generally a stand 12 rotatably connected to an appendage support frame 14. As will further be discussed herein below, the appendage support frame 14 is adapted to carry and support at least one appendage.

The stand 12 includes a platform 16 and a plurality of legs 20. The platform 16 defines a central axis 42. The legs 20 are rotatably connected to the platform 16 in a substantially radial configuration, such as to allow each of the legs 20 to pivot about the platform 16 toward the central axis 42 to a folded position and away from the central axis 42 to an open position.

Figure 2:
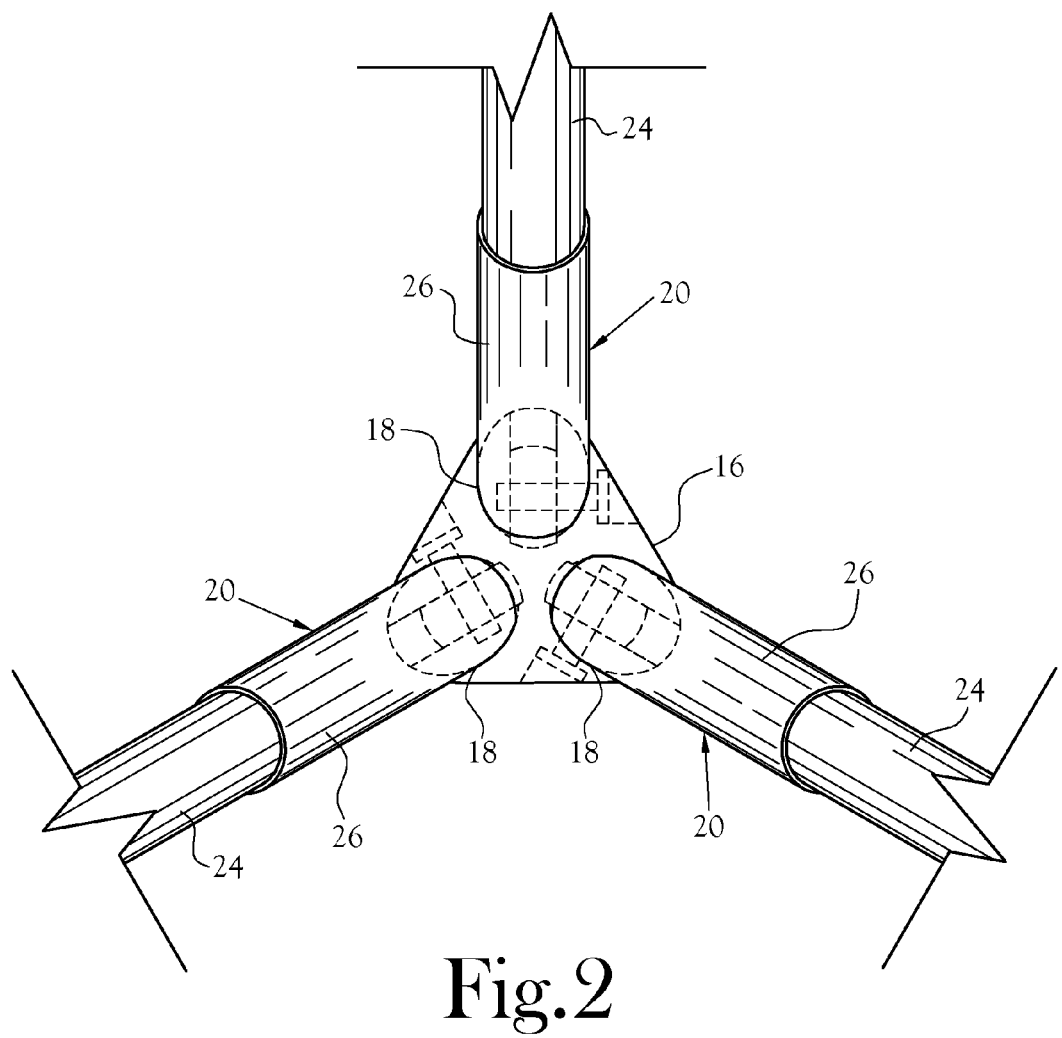
FIG. 2 is a partial bottom view of the appendage elevation support structure of FIG. 1, showing the platform and portions of the telescoping legs.

FIG. 2 illustrates a bottom view of the platform 16. In the illustrated embodiment, the platform 16 defines a plurality of sockets 18 disposed radially about the central axis 42. One leg 20 is received by each socket 18, and each leg 20 is rotatably connected to the platform 16 so as to allow the leg 20 to rotate toward, away from or otherwise about the central axis 42. Each socket 18 serves to limit the rotational range of each leg 20 between the folded and open positions. It will be understood that other devices and configurations may be used to limit the rotational range of the legs 20 without departing from the spirit and scope of the present invention. Furthermore, in the illustrated embodiment, three legs 20 cooperate with three sockets 18 defined by the platform 16 to form a collapsible tripod. However, those skilled in the art will recognize that more than three legs 20 may be provided without departing from the spirit and scope of the present invention.

Figure 3:
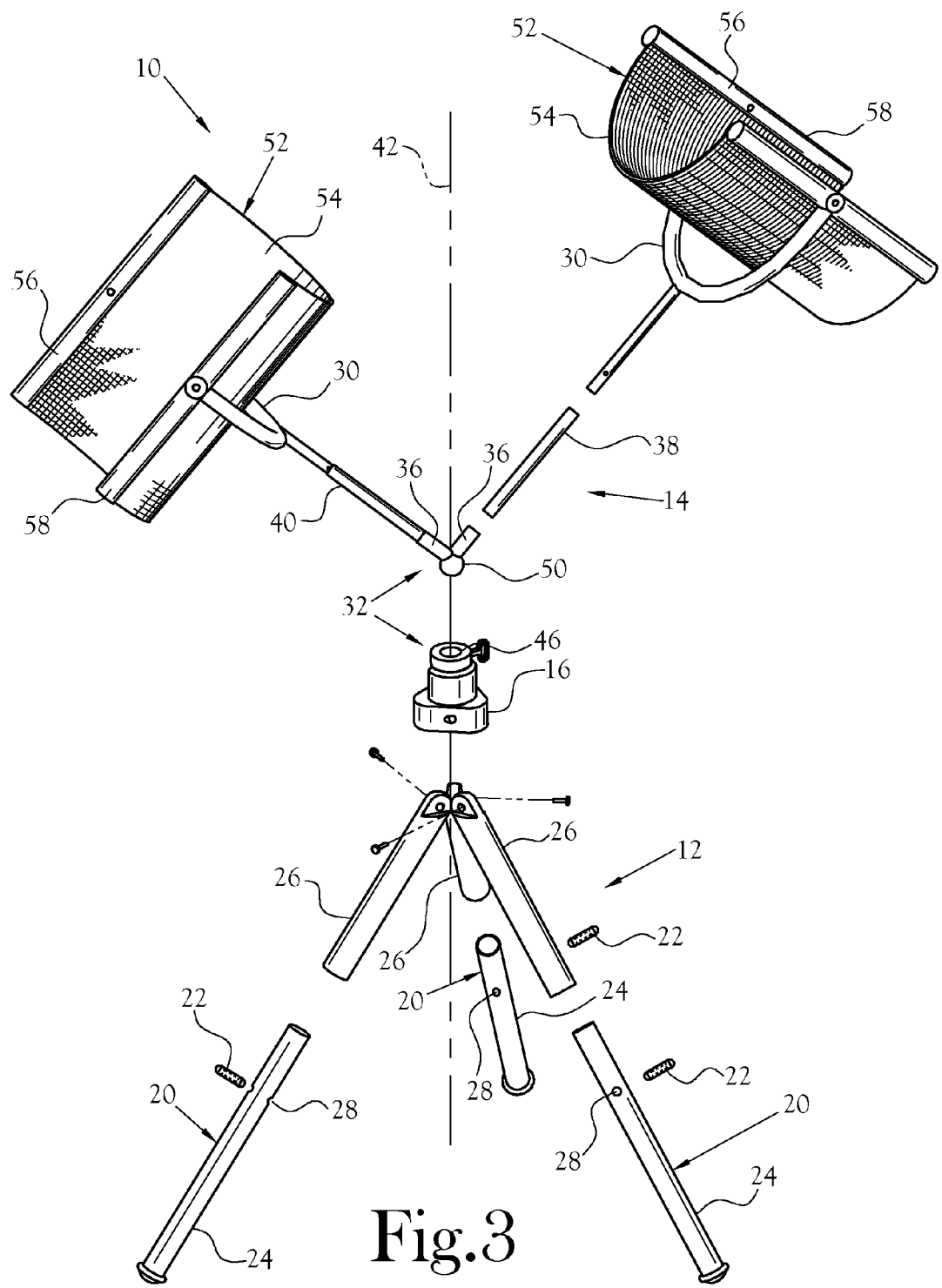
FIG. 3 is an exploded view of the appendage elevation support structure of FIG. 1.

FIG. 3 shows an exploded view of the present embodiment of the structure 10. In the present embodiment, each leg 20 is defined by a telescopically extendable member. Each leg 20 includes at least one inner telescoping member 24 slidably received within an outer telescoping member 26. Additionally, a locking mechanism is provided to lock the inner telescoping member 24 in an extended position relative to the outer telescoping member 26. In the present embodiment, each inner telescoping member 24 defines a through bore 28. The locking mechanism is a spring-loaded pin 22 slidably received within each through bore 28. Each spring-loaded pin 22 is biased toward an extended position protruding through the through bore 28. The spring-loaded pin 22 is adapted to be selectively collapsed within the inner telescoping member 24 to allow for collapse of the inner telescoping member 24 within the outer telescoping member 26. Extension of the inner telescoping member 24 relative to the outer telescoping member 26 sufficient to expose the through bore 28 results in extension of the spring-loaded pin 22 through the through bore 28, thereby locking the inner telescoping member 24 of the leg 20 in an extended position proximate the outer telescoping member 26. Those skilled in the art will recognize other suitable devices and configurations for securing the leg 20 in an extended position, and such devices and configurations may be used without departing from the spirit and scope of the present invention.

The platform 16 carries a connector 32 having a ball 50 and a socket 46. In the illustrated embodiment, the platform 16 defines the socket 46. A plurality of mounting members 36 are fixed in an angular configuration to the ball 50. The socket 46 is sized and configured to receive the ball 50 such as to allow the ball 50 to rotate within the socket 46. Those skilled in the art will appreciate that the relative positions of the ball 50 and socket 46 may be reversed such that the ball 50 is defined by the platform 16, while mounting members 36 are fixed to an independent socket 46.

Figure 4:
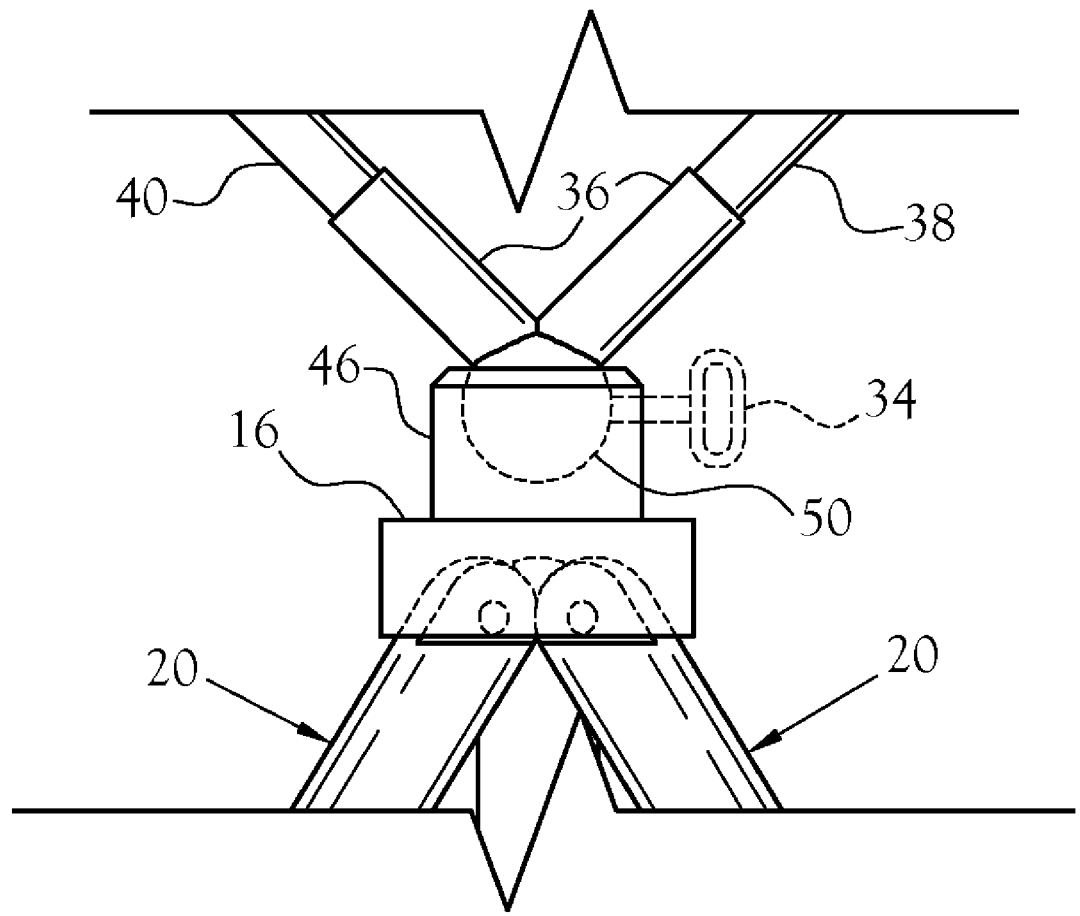
FIG. 4 is a partial side view of the appendage elevation support structure of FIG. 1.

In more discrete embodiments, a stop is provided to selectively restrain the mounting members 36 against movement proximate the platform 16. For example, in the present embodiment illustrated in FIG. 4, a bolt 34 is received by the socket 46 to selectively lock the ball 50 proximate the socket 46. In this manner, the bolt 34 restrains the mounting members 36 against rotation proximate the platform 16. In another embodiment, the ball 50 frictionally engages the socket 46 such as to limit rotation of the connector 32. Those skilled in the art will recognize other devices suitable for selectively restraining the mounting members 36 against movement proximate the platform 16 which may be used without departing from the spirit and scope of the present invention.

Referring again to FIG. 3, the platform 16 is adapted to carry the appendage support frame 14. The appendage support frame 14 includes a plurality of support members 38, 40. In the illustrated embodiment, a first support member 38 and a second support member 40 are provided. The first and second support members 38, 40 are adapted to be telescopically received by the mounting members 36. In this configuration, the support members 38, 40 are secured to the ball and socket connector 32 in an angular configuration, such as to allow the support members 38, 40 to be rotatably and pivotally connected to the platform 16. Those skilled in the art will recognize other suitable devices and configurations for securing the first support member 38 proximate the second support member 40 and for rotatably and pivotally securing the support members 38, 40 proximate the platform 16, and such devices and configurations may be used without departing from the spirit and scope of the present invention.

The support members 38, 40 are each adapted to carry and support a yoke 30. In the illustrated embodiment, a yoke 30 is secured to each of the support members 38, 40 at an end opposite the platform 16. In the illustrated embodiment, each yoke 30 is rotatably secured to a cooperating support member 38, 40 by a telescopic connection. The telescopic connection between each yoke 30 and cooperating support member 38, 40 allows each yoke 30 to be selectively extended and retracted proximate the cooperating support member 38, 40. In another embodiment, the yoke 30 is fixed proximate the cooperating support member 38, 40, and each of the support members 38, 40 is rotatably secured to the ball 50. In still another embodiment, the support members 38, 40 and cooperating yokes 30 are fixed proximate the ball 50 by an integral connection. Those skilled in the art will recognize other suitable connections and configurations suitable for arrangement of the support members 38, 40 and cooperating yokes 30 proximate the platform 16, and such connections and configurations may be used without departing from the spirit and scope of the present invention.

Figure 5:
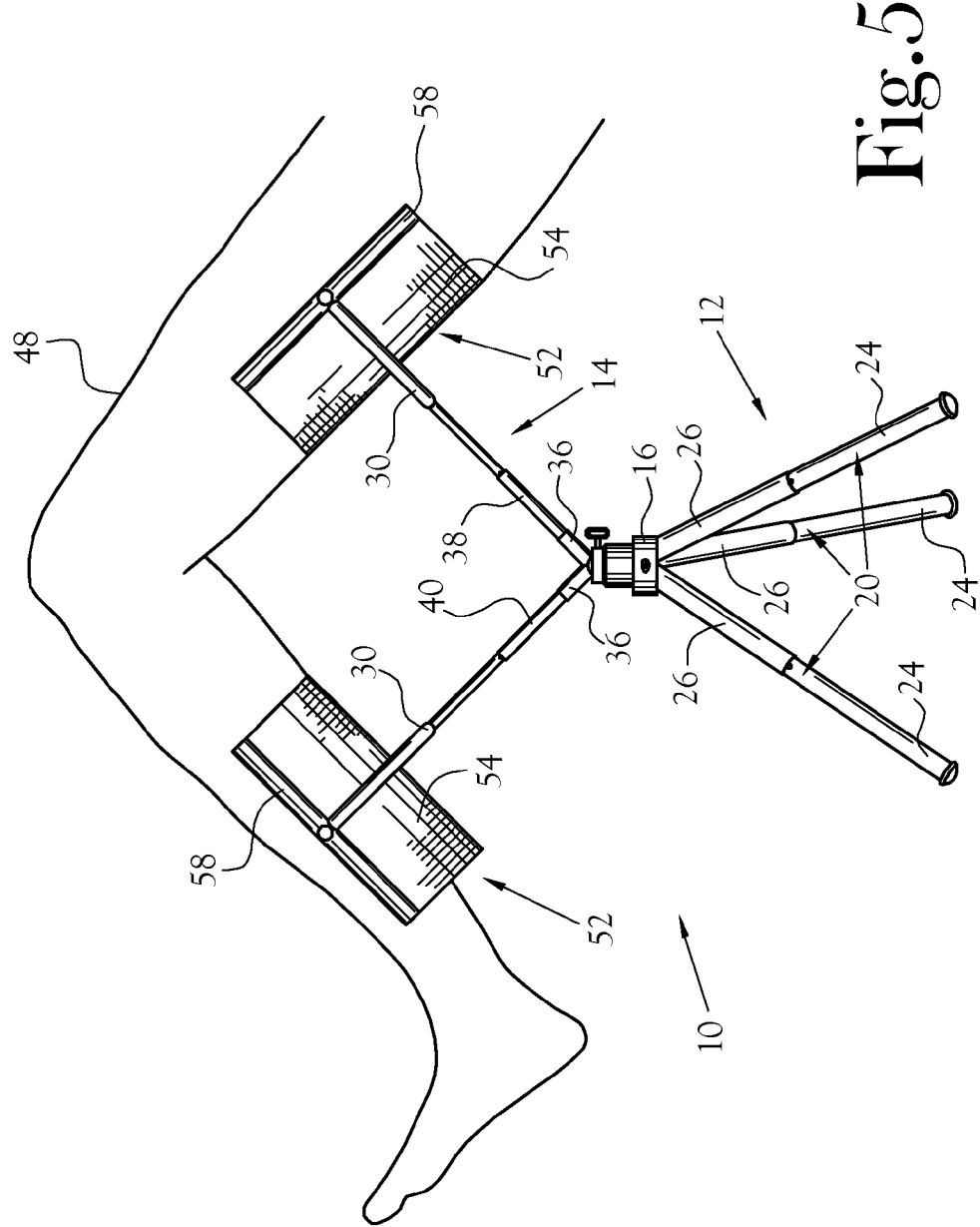
FIG. 5 is a side view of the appendage elevation support structure of FIG. 1, showing the appendage elevation support structure in an extended position and supporting an appendage in an angled position.

Each yoke 30 carries and supports a cooperating sling 52. Each sling 52 is defined by a substantially compliant sheet 54 fabricated from webbing, fabric, membrane, or the like. Each sheet 54 defines a generally rectangular shape, and includes at least a first edge supported by a first sling member 56 and a second opposite edge supported by a second sling member 58. As shown in FIGS. 5 and 8, each yoke 30 is rotatably secured to the first and second sling members 56, 58 of a cooperating sling 52 such that the yoke 30 frames and supports the sling 52 in a substantially open configuration for receiving a leg or other appendage 48. The rotatable connection between the yoke 30 and each of the first and second sling members 56, 58 allows the sling 52 to rotate within the cooperating yoke 30 to adjust to varying orientations of the appendage 48. For example, in FIG. 5, each sling 52 is rotated proximate its cooperating yoke 30 to a substantially angled configuration proximate the other sling 52, in order to accommodate the calf and thigh portions of the substantially bent leg appendage 48. By comparison, in FIG. 8 each sling 52 is rotated proximate its cooperating yoke 30 to a substantially parallel configuration proximate the other sling 52, in order to accommodate the calf and thigh portions of a substantially straightened leg appendage 48. Furthermore, in the illustrated embodiment the yokes 30 are rotatable about the cooperating support members 38, 40. Such rotation of the yokes about the cooperating support members 38, 40 further allows the slings 52 to be selectively aligned to adjust to the varying orientation of the appendage 48.

FIGS. 5 and 8 illustrate one application of the present embodiment of the structure 10. As shown in FIG. 5, in one application of the structure 10, the various legs 20 of the stand 12 are extended and rotated proximate the platform 16 to a substantially open position. Each yoke 30 and cooperating sling 52 is secured to a cooperating support member 38, 40, and each support member 38, 40 is secured to a cooperating mounting member 36. In this configuration, the stand 12 is adapted to support the appendage support structure 14 in an elevated configuration above a surface (not shown). The slings 52 are cooperatively adapted to carry and support at least one appendage 48. Referring to FIGS. 5 and 8, rotation of the slings 52 proximate cooperating yokes 30 and rotation of yokes along the linear dimension of cooperating support members 38, 40 allow the slings 52 of the appendage support structure 14 to be selectively configured to accommodate variously positioned appendages for elevated support.

Figures 6A, 6B:
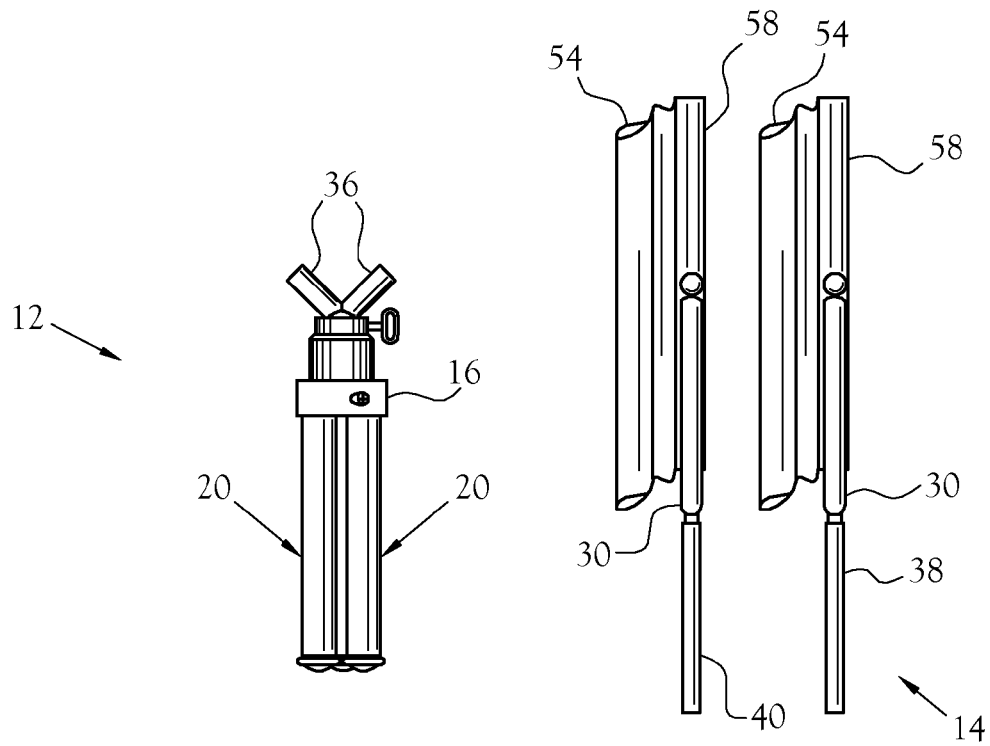
FIGS. 6A and 6B are side views showing the appendage elevation support structure in a collapsed position.

As shown in FIGS. 6A and 6B, the structure 10 is adapted to be selectively collapsed to facilitate transportation and storage of the structure 10. The stand 12 is adapted to be selectively removed from the appendage support structure 14 by selectively disconnecting the support members 38, 40 from the mounting members 36. The stand 12 is selectively collapsed by rotating the legs 20 proximate the platform 16 to a substantially collapsed position, and by selectively collapsing each leg 20 by sliding each inner telescoping member 24 within each outer telescoping member 26. In the illustrated embodiment, the telescopic connection between each yoke 30 and cooperating support member 38, 40 is selectively collapsed. Each sling member 56, 58 is selectively rotated to a substantially parallel configuration with the cooperating yoke 30. In this configuration, the appendage support structure 14 is selectively collapsed. It will be understood by one skilled in the art that the particular selective collapsibility of a specific embodiment of the structure 10 is dependant upon the particular types of connections provided between the various components of the structure. Therefore, those skilled in the art will recognize other suitable configurations allowing for selective collapsibility of the structure 10, and such other configurations may be used without departing from the spirit and scope of the present invention.

Figure 7:
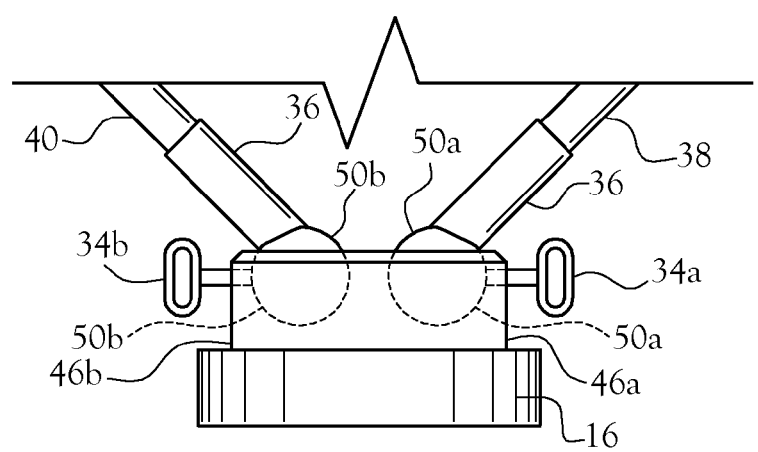
FIG. 7 is a partial side view of another embodiment of the appendage elevation support structure.

A portion of another embodiment of the structure 10 is illustrated in FIG. 7. In the embodiment of FIG. 7, a compound ball and socket connector is provided. The platform 16 defines a first socket 46a and a second socket 46b. The first socket 46a is adapted to receive a first ball 50a, and the second socket 46b is adapted to receive a second ball 50b. One mounting member 36 is fixed to each of the first and second balls 50a, 50b. In this configuration, each ball 50a, 50b is independently rotatable within its cooperating socket 46a, 46b. Thus, each mounting member 36 is selectively rotatable about the platform 16 independent of the other mounting member 36, thereby allowing for selective adjustment of the angular configuration between the mounting members 36. In the illustrated embodiment, two bolts 34a, 34b are provided. Each bolt 34a, 34b is disposed to selectively engage one ball 50a, 50b, respectively. In this configuration, the bolts 34a, 34b allow for selective immobilization of either ball 50a, 50b proximate the platform 16. Those skilled in the art will recognize other configurations suitable to accomplish the ball and socket connector 32, and such configurations may be used without departing from the spirit and scope of the present invention.

While the present invention has been illustrated by description of several embodiments and while the illustrative embodiments have been described in detail, it is not the intention of the applicant to restrict or in any way limit the scope of the appended claims to such detail. Additional modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicants general inventive concept.

Having thus described the aforementioned invention, what is claimed is:

1. An appendage elevation support structure comprising:
a platform defining a central axis;
a plurality of legs for supporting said platform above a surface, each of said plurality of legs being secured to said platform in a substantially radial configuration about said central axis;
a frame carried by said platform, said frame having a plurality of support members including at least a first support member and a second support member, wherein said frame further comprises a plurality of yokes, each of said plurality of yokes being carried by at least one of said support members; and
a plurality of slings adapted to cooperate to cradle and support a human appendage, each of said plurality of slings being carried and supported by said frame, wherein each of said plurality of slings comprises a substantially compliant sheet defining at least a first edge and a second opposite edge, said sheet being supported along said first edge by a first sling member and along said second opposite edge by a second cooperating sling member, each of said plurality of yokes being secured to cooperating first and second sling members of one of said plurality of slings such as to carry said sling in a substantially open configuration;
wherein each of said plurality of yokes is telescopically secured to one of said support members such as to allow each of said yokes to be selectively extendable and retractable proximate said corresponding support member and to allow each of said yokes to be rotatable along a linear dimension of said corresponding support member.

2. An appendage elevation support structure comprising:
a platform defining a central axis, wherein said platform defines a socket of a ball and socket connector;
a plurality of legs for supporting said platform above a surface, each of said plurality of legs being secured to said platform in a substantially radial configuration about said central axis;
a frame carried by said platform, said frame having a plurality of support members including at least a first support member and a second support member, said frame defining a ball of said ball and socket connector, said ball being adapted to be received by said socket;
a plurality of mounting members fixed to said ball, each of said mounting members being adapted to secure one of said support members to said ball in a substantially angular configuration proximate another of said support members; and
a plurality of slings adapted to cooperate to cradle and support a human appendage, each of said plurality of slings being carried and supported by said frame wherein each of said plurality of slings comprises a substantially compliant sheet defining at least a first edge and an opposite edge, said sheet being supported along said first edge by a first sling member and along said opposite edge by a second cooperating sling member, and wherein each of said plurality of mounting members is adapted to telescopically connect to one of said support members.

3. The appendage elevation support structure of claim 2 wherein said frame further comprises a plurality of yokes, each of said plurality of yokes being carried by at least one of said support members, each of said plurality of yokes being secured to cooperating first and second sling members of one of said plurality of slings such as to carry said sling in a substantially open configuration.

4. The appendage elevation support structure of claim 3 wherein each of said plurality of yokes is rotatably secured to said cooperating first and second sling members of one of said plurality of slings such as to allow said sling to rotate within said corresponding yoke.

5. The appendage elevation support structure of claim 3 wherein each of said plurality of yokes is telescopically secured to one of said support members such as to allow each of said yokes to be selectively extendable and retractable proximate said corresponding support member and to allow each of said yokes to be rotatable along a linear dimension of said corresponding support member.

6. An appendage elevation support structure comprising:
a frame having a plurality of support members including at least a first support member and a second support member;

a plurality of slings adapted to cooperate to cradle and support a human appendage, each of said plurality of slings being carried and supported by said frame; and a stand for carrying said frame, said stand being rotatably and pivotally secured to said frame;

wherein each of said plurality of slings comprises a substantially compliant sheet defining at least a first edge and an opposite edge, said sheet being supported along said first edge by a first sling member and along said opposite edge by a second cooperating sling member, said appendage elevation support structure further comprising:

a ball, each of said plurality of mounting members being fixed to said ball in an angular configuration proximate another of said plurality of mounting members;

a socket carried by said stand, said socket being adapted to receive said ball such as to rotatably and pivotally secure said plurality of support members to said stand;

a plurality of yokes, each of said plurality of yokes being carried by at least one of said plurality of support members, each of said plurality of yokes being rotatably secured to said first and second sling members of a cooperating sling such that each of said yokes frames and supports said cooperating sling in a substantially open configuration.

7. The appendage elevation support structure of claim 6 wherein each of said plurality of yokes is rotatably secured to one of said plurality of support members.

8. The appendage elevation support structure of claim 6, wherein each of said plurality of yokes is telescopically connected to one of said plurality of support members.

* * * * *